US009039687B2

United States Patent
Condie et al.

(10) Patent No.: US 9,039,687 B2
(45) Date of Patent: May 26, 2015

(54) REACTANCE CHANGES TO IDENTIFY AND EVALUATE CRYO ABLATION LESIONS

(75) Inventors: Catherine R. Condie, Shoreview, MN (US); Kathryn Elaine Kasischke, San Diego, CA (US); Marshall L. Sherman, Cardiff by the Sea, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1213 days.

(21) Appl. No.: 12/914,782

(22) Filed: Oct. 28, 2010

(65) Prior Publication Data

US 2012/0109115 A1     May 3, 2012

(51) Int. Cl.
| | |
|---|---|
| *A61B 18/08* | (2006.01) |
| *A61B 5/053* | (2006.01) |
| *A61B 17/00* | (2006.01) |
| *A61B 18/00* | (2006.01) |
| *A61B 18/02* | (2006.01) |
| *A61B 18/14* | (2006.01) |

(52) U.S. Cl.
CPC ..... *A61B 5/0538* (2013.01); *A61B 2017/00026* (2013.01); *A61B 2018/00755* (2013.01); *A61B 2018/0262* (2013.01); *A61B 2018/1407* (2013.01); *A61B 2018/1467* (2013.01)

(58) Field of Classification Search
CPC ............... A61B 2018/0022; A61B 2018/0212; A61B 2018/0262; A61B 2018/128; A61B 2018/1467; A61B 2017/00026; A61B 5/0538; A61B 2018/00875
USPC .................... 606/20–23, 34; 607/96, 105, 113
See application file for complete search history.

(56) References Cited

U.S. PATENT DOCUMENTS

| | | | |
|---|---|---|---|
| 6,235,018 B1 * | 5/2001 | LePivert | .......................... 606/20 |
| 6,696,844 B2 | 2/2004 | Wong et al. | |
| 2003/0158477 A1 | 8/2003 | Panescu | |
| 2005/0010202 A1 | 1/2005 | Podany et al. | |
| 2008/0200828 A1 * | 8/2008 | Abboud et al. | ............... 600/547 |
| 2009/0171345 A1 | 7/2009 | Miller et al. | |
| 2009/0182318 A1 | 7/2009 | Abboud et al. | |

FOREIGN PATENT DOCUMENTS

| | | |
|---|---|---|
| CN | 1895166 A | 1/2007 |
| CN | 101534736 A | 9/2009 |
| WO | 02102263 A1 | 12/2002 |
| WO | 2007138552 A2 | 12/2007 |

OTHER PUBLICATIONS

The State Intellectual Property Office of the People's Republic of China, Oct. 23, 2014 Notice on the First Office Action, Application No. 201180051139.3, 10 pages.

* cited by examiner

*Primary Examiner* — Michael Peffley
*Assistant Examiner* — Thomas Giuliani
(74) *Attorney, Agent, or Firm* — Christopher & Weisberg, P.A

(57) ABSTRACT

A method of assessing lesion quality of an ablated tissue region comprising ablating at least a portion of the tissue region. The reactance of the ablated tissue region is measured at a plurality of frequencies. The lesion quality of the ablated tissue region is determined based on the measured reactance. For example, an untreated tissue reactance value and a predetermined thermally treated tissue region reactance threshold may be determined. The measured reactance at each of the plurality of frequencies is compared to the threshold to determine the lesion quality of the thermally treated tissue region. The thermal treatment of the tissue may be modified based on the lesion quality determination.

8 Claims, 6 Drawing Sheets

Figure 1: Bipolar lesion depth with cryo pretreatment compared to control.

|  | Control | Cyro | P Value |
| --- | --- | --- | --- |
| % Lesion Depth | 30.9 ± 12.0 | 59.0 ± 15.1 | 0.01 |
| Mag Impedance ($\Omega$) | 20.5 ± 1.9 | 18.4 ± 1.3 | 0.09 |
| Reactance ($\Omega$) | -8.1 ± 1.1 | -3.9 ± 1.0 | <0.001 |
| Resistance ($\Omega$) | 18.8 ± 2.0 | 18.0 ± 1.4 | 0.4 |

Table 1: Impedance values and lesion depth of tissue with cryo pretreatment followed by RF delivery compared to control using bipolar RF energy.

Figure 1: Unipolar lesion depth with cryo pretreatment compared to control.

| | Control | Cyro | P Value |
|---|---|---|---|
| Lesion Depth (mm) | 2.7±0.8 | 3.6±1.2 | 0.3 |
| Mag Impedance (Ω) | 22.4±3.8 | 19.3±3.1 | 0.3 |
| Reactance (Ω) | -7.6±3.6 | -4.0±3.1 | 0.03 |
| Resistance (Ω) | 21.0±2.8 | 18.7±2.9 | 0.4 |

Table 1: Impedance values and lesion depth of tissue with cryo pretreatment followed by RF delivery compared to control using unipolar energy.

REACTANCE CHANGES TO IDENTIFY AND EVALUATE CRYO ABLATION LESIONS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method for measuring and correlating changes in reactance of cryogenically treated tissue to assess lesion quality and transmurality.

BACKGROUND OF THE INVENTION

Radiofrequency (RF) and cryogenic ablation procedures are well recognized treatments for vascular and cardiac diseases such as atrial fibrillation. The application of either RF or cryogenic treatment is usually based on the preference of the surgeon or the specific tissue to be treated. In either RF or cryogenic ablation, however, the location and quality of the lesion produced is a primary concern.

Current methods to identify a lesion's location and assess its quality include coupling a plurality of electrodes to the distal end of a medical device proximate a tissue to be treated, applying a voltage, and measuring impedance across the electrodes with the tissue to be treated completing the circuit. Electrical impedance is defined as the total opposition to alternating current by an electric circuit, equal to the square root of the sum of the squares of the resistance and reactance of the circuit and usually expressed in ohms. In general, the impedance decreases as the treated tissue becomes necrotic. As such, impedance may be used to identify particular areas which have been treated and those that have not.

One drawback to impedance tomography is its lack of direct feedback to evaluate whether a lesion was successfully created to the desired transmurality, quality, or continuity. In particular, impedance measurements provide binary data regarding a particular lesion; either the tissue is viable or necrotic. Impedance measurements alone, however, do not provide real-time assessment of whether a cryogenic or RF lesion was successfully created to a desired lesion depth, in part, because different tissue levels have different impedances.

As such, it would be desirable to provide improved methods of assessing lesion quality and depth of cryogenically and/or RF treated tissue to determine the efficacy and resulting characteristics of the treatment.

SUMMARY OF THE INVENTION

The present invention advantageously provides a method of assessing lesion quality of an ablated tissue region comprising ablating at least a portion of the tissue region; measuring the reactance of the ablated tissue region; and determining the lesion quality of the ablated tissue region based on the measured reactance.

In another embodiment, the method includes positioning a medical device proximate the tissue region and circulating coolant towards a thermally conductive region of the medical device, the medical device having at least two electrodes, the electrodes being positioned proximate the thermally conductive region; thermally treating the tissue region; inducing a current between the at least two electrodes at a plurality of frequencies; measuring the reactance of the thermally treated tissue region at each of the plurality of frequencies; defining a predetermined thermally treated tissue region reactance threshold; comparing the measured reactance at each of the plurality of frequencies to the threshold; determining the lesion quality of the thermally treated tissue region based on the measured reactance at each of the plurality of frequencies; and modifying the thermally treating of the tissue based at least in part on the determination.

In yet another embodiment, the method includes positioning a medical device proximate the tissue region and circulating coolant toward a thermally conductive region of the medical device, the medical device have at least two electrodes, the at least two electrodes being position proximate the thermally conductive region, the medical device further having a balloon disposed between the two electrodes; cryogenically cooling the tissue region; inducing a current between the at least two electrodes at a plurality of frequencies; measuring the reactance of the cryogenically cooled tissue region at each of the plurality of frequencies; defining a predetermined thermally treated tissue region reactance threshold; defining an untreated tissue reactance value, wherein the predetermined thermally treated tissue region reactance threshold is about a 60-90% reduction in the reactance of the untreated tissue reactance value; comparing the measured reactance to the threshold; determining the lesion quality and continuity of the thermally treated tissue region based on the comparison; displaying the determined lesion quality and continuity on an imaging system; and modifying the circulating coolant toward a thermally conductive region of the medical device based on the displayed tissue quality and continuity.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
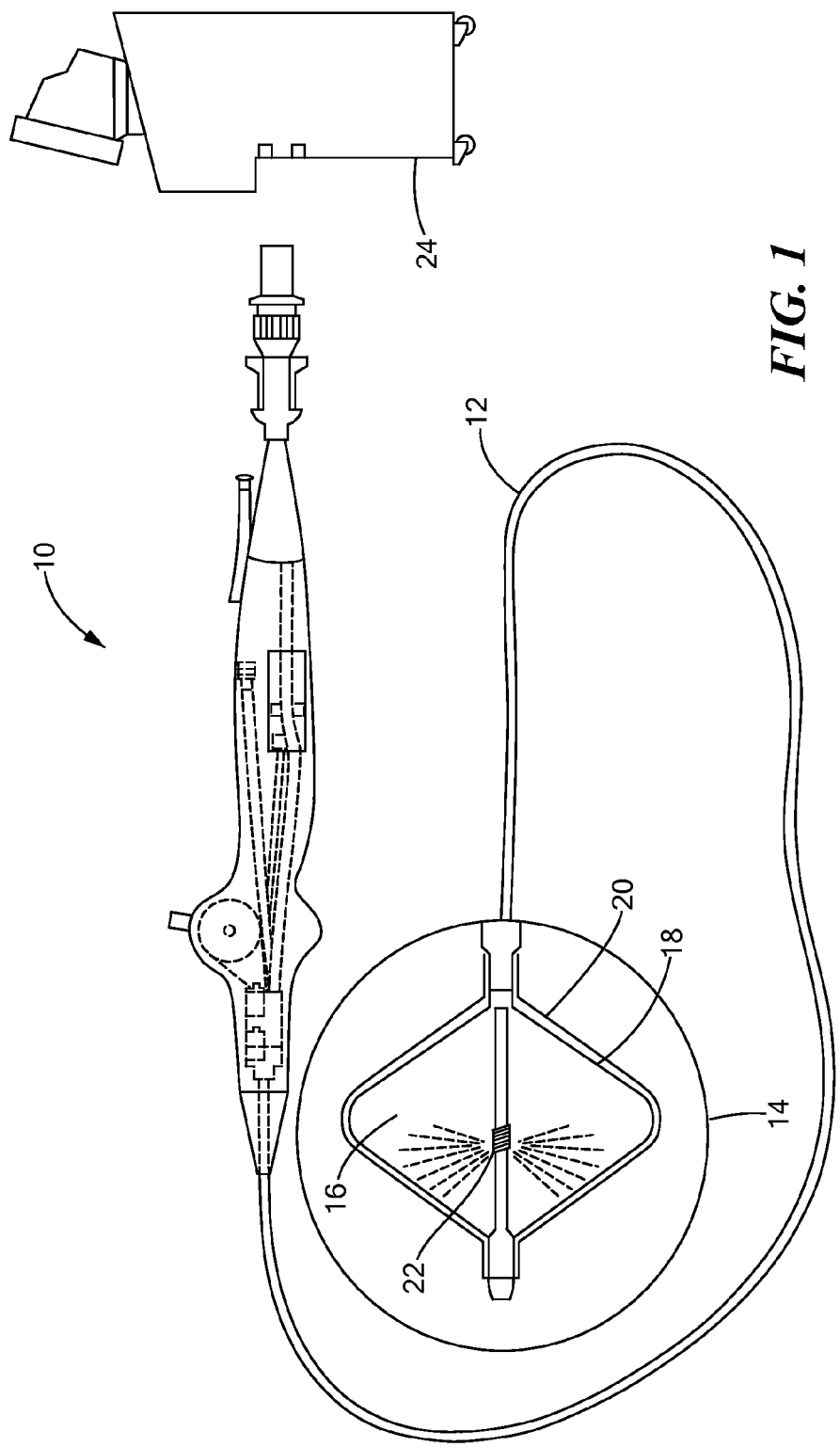
FIG. 1 illustrates an exemplary cryogenic ablation medical system and device in accordance with the method of the present invention.

Now referring to the figures in which like reference designators refer to like elements, there is shown in FIG. 1 an exemplary medical system and device used for exchanging cryogenic ablation energy and used in accordance with an exemplary method of the present invention and designated generally as "10." The medical device 10 may be an elongate, highly flexible and deflectable cryogenic ablation catheter that is suitable for passage through the vasculature or to be applied epicardially through a surgical incision. The medical device 10 may further include a catheter body 12 having a distal end 14 with a thermally conductive region 16 at or proximal to the distal end 14.

Figure 2:
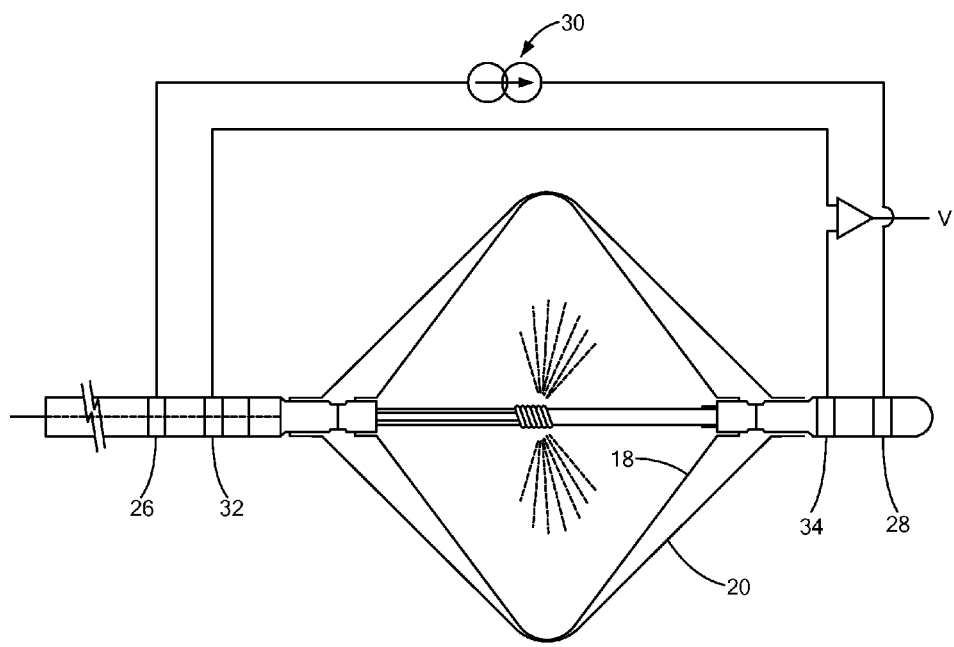
FIG. 2 illustrates an embodiment of a distal end of the catheter system shown in FIG. 1 having a plurality of electrodes.

The thermally conductive region 16 is shown in FIG. 1 and FIG. 2 as a double balloon having a first membrane (e.g., inner balloon) 18 contained or enclosed within a second membrane (e.g., outer balloon) 20. The thermally conductive region 16 may include a single balloon, multiple balloons in series, and/or a linear, coiled, or curvilinear thermally conductive segment. Alternatively, the medical device 10 may be a surgical clamp (not shown) including a flexible or rigid shaft having a first jaw and as second, either or both jaws having a thermally conductive region 16 which includes a cryogenic ablation element.

The medical device may include one or more coolant supply tubes 22 in fluid communication with a coolant supply in a console 24. The coolant may be released into one or more openings (not shown) in the tube 22 within the inner balloon 18 (or other cryogenic ablation element) in response to console 24 commands and other control input. As the fluid egresses into the inner balloon 18, the fluid expands and cools by the Joule-Thompson effect occurring at the distal end 14 of the medical device 10. The console 24 may include one or more sensors or controls (not shown) for initiating or triggering one or more alerts or therapeutic delivery modifications during operation of the medical device 10. One or more valves, controllers, or the like may be in communication with the sensor(s) to provide for the controlled dispersion or circulation of fluid through the coolant supply tubes 22. Such valves, controllers, or the like may be located in a portion of the medical device 10 and/or in the console 24.

The medical device 10 may further include the ability to assess tissue contact, lesion quality, fluid egress and/or tip ice coverage. For example the medical device 10 include a first pair of electrodes (26, 28) disposed about the outer balloon 20. The electrodes (26, 28) may both be disposed on either side of the outer balloon 20 or the outer balloon may be disposed between them as shown in FIG. 2. The electrodes (26, 28) may be in electrical communication with a power source (not shown) to apply a providing a excitation current 30 of a selected amplitude (e.g., in the range of 0.2 mA to 5 mA) and frequency (e.g., in the range of 10 kHz to 1 MHz) to create a current field and measuring the differential reactances as produced across a second pair of electrodes (32, 34). For example, as shown in FIG. 2, a voltage "V" is applied between the electrodes (26, 28) and the reactance is measured across electrodes (32, 34). The medical device 10 may be positioned such that the outer balloon 20 is positioned proximate the tissue to be treated with the electrodes (26, 28) and (32, 34) disposed on opposite sides of the treatment region. Alternatively, the medical device 10 may be navigated to a position such that the outer balloon 20 is adjacent the tissue region to be treated and the reactance of healthy tissue is measured.

Figure 3:
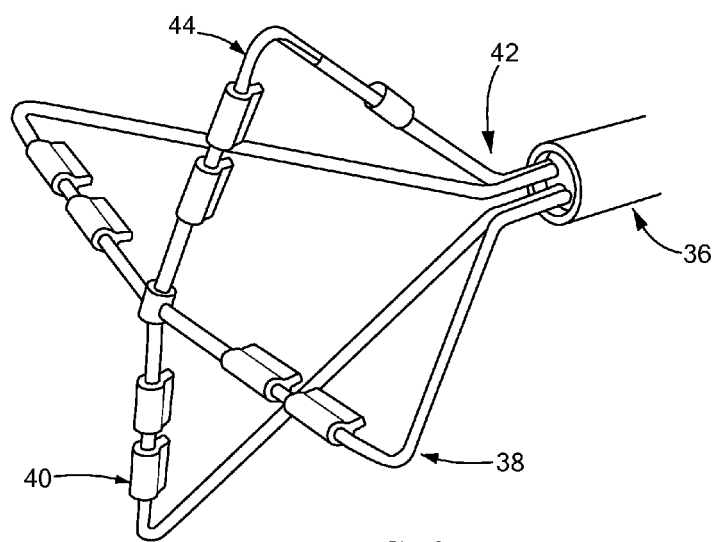
FIG. 3 illustrates an exemplary radiofrequency ablation device in accordance with the method of the present invention.

The medical device 10, or a second medical device 36 (FIG. 3), may further be in electrical communication with a power source (not shown) that delivers RF ablation energy to one or more electrodes 40 coupled to a distal end 38 of the second medical device 36. Alternatively, the power source may deliver RF ablation energy to electrodes (26, 28) and/or electrodes (32, 34) such that RF ablation energy may be delivered between two adjacent electrodes. The second medical device 36 device may be a RF ablation catheter including a carrier assembly 42 having one or more carrier arms 44 each having one or more electrodes 40 coupled to it. The electrodes 40 may be arranged in series along each carrier arm 44 such that RF ablation energy may be transmitted between two adjacent electrodes 40 and transmitted to the region of tissue to be treated. Optionally, a back plate ground electrode (not shown) may be positioned beneath the patient during treatment such that when power is delivered to medical device 10 or the second medical device 36, RF ablation energy may be transmitted from electrodes (26, 28) and/or electrodes (32, 34) or electrodes 40 to the back plate.

The carrier assembly 42 may further define an umbrella tip when expanded and may fully expand from and retracted with in catheter body 12. As such, the electrodes 40 may be bent and/or deflected, along with the carrier arms 44, to define a myriad of shapes to ablate tissue. Alternatively, the second medical device 36 may be a RF ablation clamp operable to make a substantially circumferential ablation lesion around the tissue to be treated or a "pen" like device.

Figure 4:
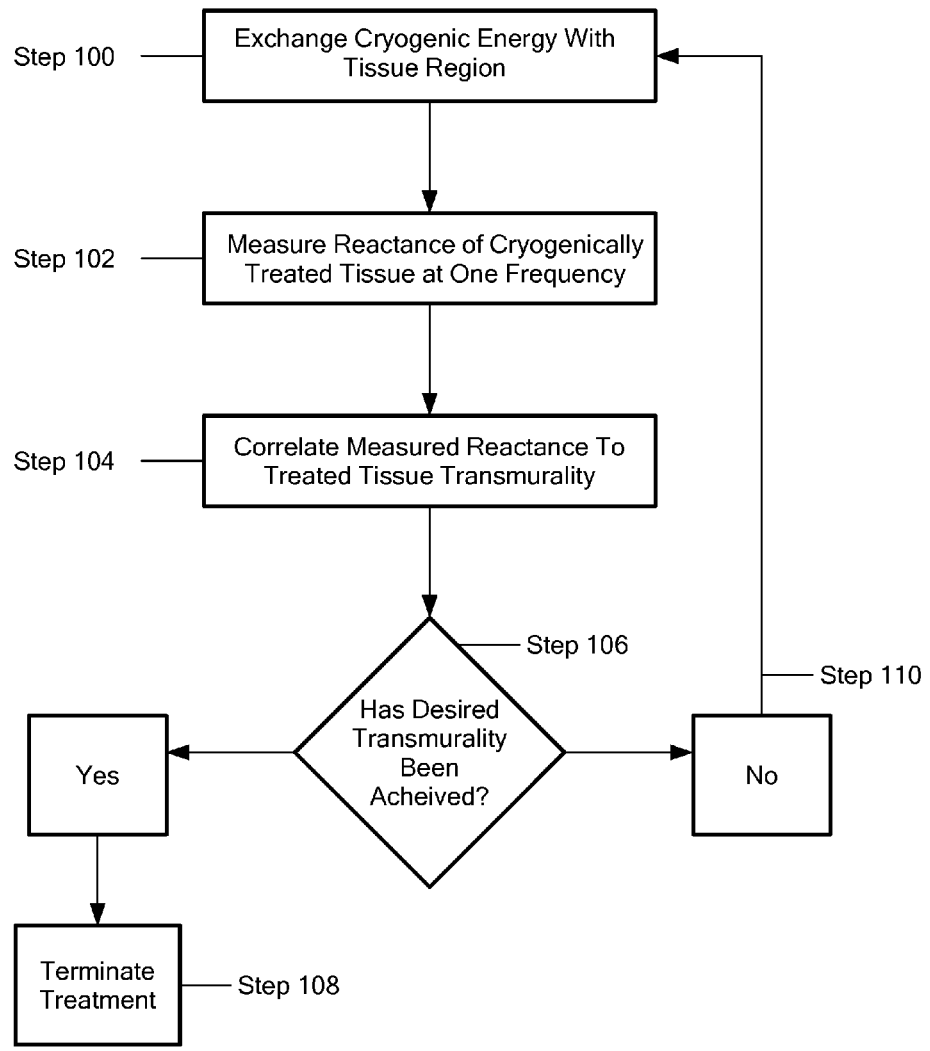
FIG. 4 is a flow chart of an exemplary method in accordance with the principles of the present invention.

Now referring to FIG. 4, where an exemplary method of assessing lesion quality is shown. The method includes exchanging cryogenic ablation energy with a region of tissue such that the region of tissue is ablated and/or cooled (Step 100). For example, medical device 10 may be positioned proximate the region of tissue to ablated. A cryogenic fluid may then be circulated towards the thermally conductive region 16 where it delivers cryogenic energy to the target tissue region. The cryogenic energy may be exchanged with a region of tissue for a time period of, for example, 1-5 minutes. Alternatively, cryogenic ablation energy may be exchanged for a time period of, two minutes, followed by a two minute thaw period, where no cryogenic energy is exchanged, followed by an additional minute of cryogenic energy being exchanged. In an exemplary embodiment, the temperature of the cryogenic ablation element and/or contacted tissue is reduced to approximately −55° C. to −60° C. The cryogenic energy may be exchanged with the region of tissue by any of the medical device embodiments discussed above and with any tissue region, for example, the atrial valve or vasculature.

Following the exchange of cryogenic energy, the reactance or resistance of the treated tissue region may be measured (Step 102). For example, as a current is induced between electrodes (26, 28) and/or electrodes (32, 34) or electrodes 40, the opposition of the ablated tissue region to a change in current, known as reactance, is measured. As the tissue is ablated, the reactance decreases as the opposition to the current decreases. Optionally, the reactance of the tissue adjacent the treated tissue region may also be measured to prevent unwanted tissue from being ablated. The reactance may be measured at one or more excitation frequencies, for example, 10 kHz, 470 kHz, and 1 MHz. By measuring the reactances at one or more excitation frequencies, the magnitude of the percentage of reduction in reactance for each time period at each frequency may be measured. For example, at higher frequencies, for example, 1 MHz, the destruction of the cellular membrane may be detected in the form of a change in reactance and compared to a change in reactance at lower frequencies. The change in the reactance of the cryogenically treated tissue region may then be correlated to determine and assess the transmurality of the tissue region (Step 104). As used herein, the term "transmurality" means the depth or distance a lesion or ablated tissue passes through the wall of the tissue region. For example, tissue treated with cryogenic energy for five minutes exhibits a larger decrease in reactance, which can be correlated to the destruction of cellular membranes and to tissue transmurality.

Further, at particular frequencies the correlation between reactance and transmurality may be stronger than that of measurement of impedance, thus allowing for an accurate and real-time assessment of the quality of the cryogenic lesion. Similarly, the time rate of change in reactance or resistance measured at particular frequencies may be correlated to the depth of a lesion because the time rate of change of resistance during the treatment procedure, for example, may correspond to how quickly the tissue freezes. The measured ablated tissue region transmurality may then be compared to a predetermined ablated tissue region transmurality or reactance threshold. (Step 106). If the desired transmurality is achieved, (e.g., the treatment transmurality threshold is reached), treatment may be modified or stopped, for example, by terminating the delivery of coolant to the thermally conductive region 16. (Step 108) If the desired transmurality has not been achieved, cryogenic ablation energy may be delivered for an additional time period (Step 110).

Figure 5:
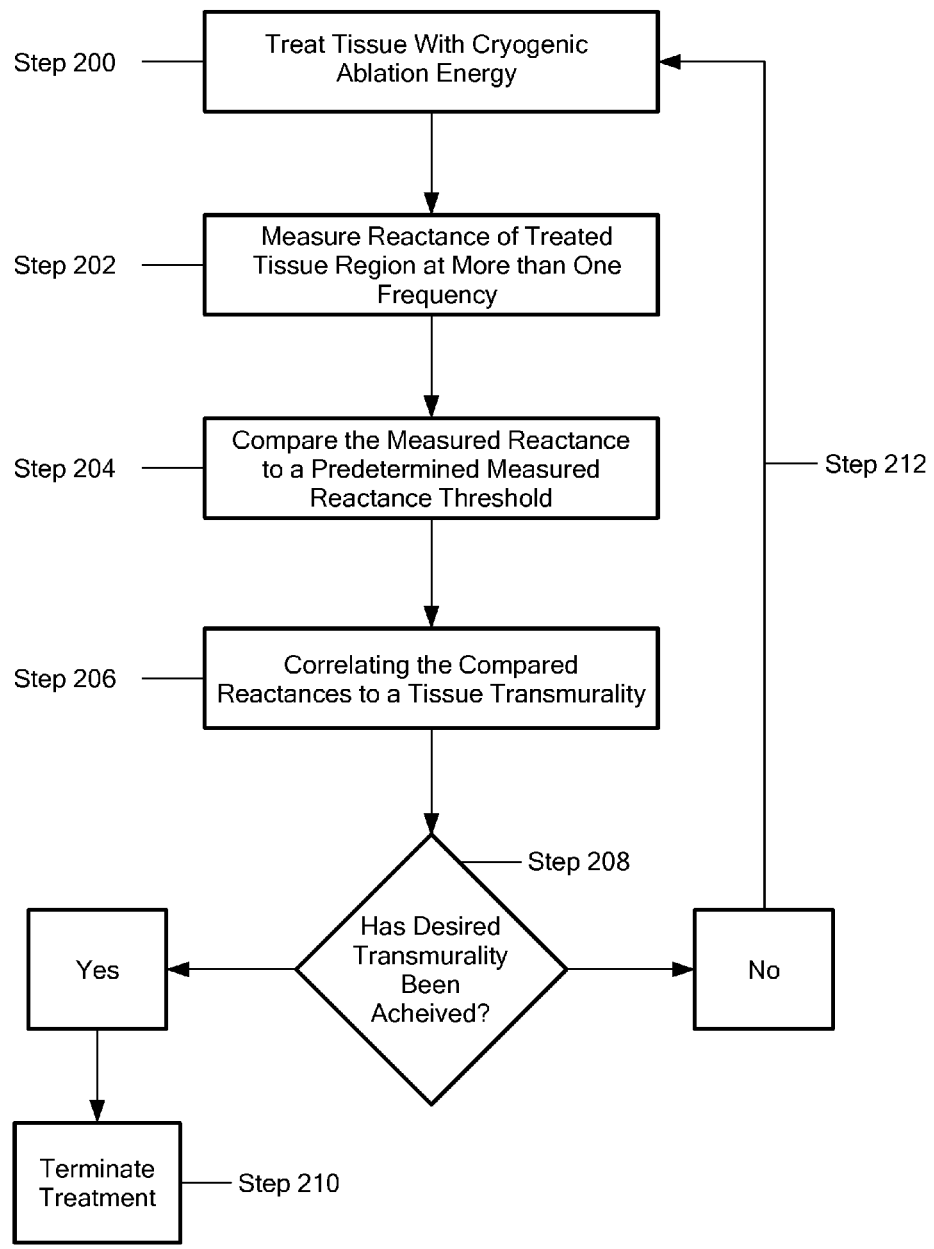
FIG. 5 is flow chart of another exemplary method in accordance with the principles of the present invention.

Now referring to FIG. 5, where another method of assessing the quality of a lesion includes exchanging cryogenic ablation energy with a tissue region. The method includes pretreating the tissue region with cryogenic ablation energy for any time period, such as, for example, approximately five minutes by the method discussed above. (Step 200). Optionally, either a fluoroscopic or a non-fluoroscopic navigation system may be used to track one or more of electrodes (for example, electrodes 40, electrodes 26 and 28 and/or electrodes 32 and 34) and a reference electrode (not shown) disposed on the medical device 10 or the second medical device 36, such that the location of the medical device 10 or the second medical device 36 may be graphically displayed during the pretreatment of the tissue region.

The reactance of the ablated tissue region may then be measured at a plurality of frequencies, simultaneously with or sequentially after the pretreatment (Step 202). The time rate of change of the measured reactance may also be measured during the pretreatment to determine when the tissue region is covered with ice. The measured reactance may be compared to a predetermined ablated, treated, or cooled tissue region reactance or transmurality threshold, which may be selected prior to the treatment. (Step 204). For example, the medical device 10 may include a particular reactance or transmurality threshold, for example, a 60-90% decrease in reactance of treated tissue as compared to the reactance of untreated tissue may be indicative of a quality lesion, which may be device specific and correlated to a particular transmurality. In particular, a baseline reactance of untreated tissue may be defined before or measured during the thermal treatment of the tissue region. The baseline reactance measurement may then be compared to the measured reactance to determine the percent decrease in the reactance of the treated tissue.

The measured reactances over at the plurality of frequencies may then be correlated to determine and assess the lesion depth, transmurality, or continuity. (Step 206). For example, lesion quality may be assessed by calculating a tissue transmurality based on the compared measured reactance. Alternatively, the reactance measurements recorded at each of the plurality of applied RF frequencies may be compared and correlated to tissue transmurality. If the desired transmurality is achieved (Step 208), for example, the treatment transmurality threshold is reached and treatment may be modified or stopped. (Step 210). If the desired transmurality is not achieved, the tissue region may be treated with additional cryogenic energy and the method may recycle. (Step 212). Alternatively, RF ablation energy may be delivered to the cryogenically pretreated tissue region immediately following the delivery of cryogenic energy while the reactance is measured. For example, the reactance may be remeasured and correlated to tissue transmurality after the RF ablation energy is transmitted to the tissue region.

Additionally, the correlated transmurality may be used to determine if a contiguous lesion was successfully created. For example, gaps in a lesion may be detected by measuring the reactance at one or more frequencies. In particular, the measurement of reactance at higher frequencies may be more sensitive to slight changes in reactance to aid in identifying lesion gaps. If there is no change in the measured reactance, a lesion may not have been created at a desired location. In particular, a plurality of reactance measurements may be made at a variety of different locations at a particular treatment region. As such, the measured reactance at each of many locations can be correlated to determine a lesion's shape, quality, and transmurality.

Additionally, the measured reactance and/or correlated tissue quality or transmurality data may be displayed numerically and/or graphically on a display or the console 24 during the procedure. For example, the determined transmurality or continuity data may be graphically displayed and treatment may be modified based on the displayed transmurality. As such, gaps may be detected in a lesion and displayed for the physician. Optionally, the tissue quality, reactance, and/or transmurality data may be recorded and stored remotely in a database. For example, previously recorded data may be compared to current data to assess treatment efficacy and monitor patient progress. As such, it is contemplated that treatment models may be created based on historical and present reactance, quality, and tissue transmurality data.

The delivery of RF energy for measuring reactance may include unipolar and/or bipolar RF modalities. For example, a current may be induced and a voltage applied between two adjacent electrodes 40 on the second medical device 36 such that RF energy is transmitted between them. Alternatively, when power is delivered to medical device 10 or the second medical device 36, RF energy may be transmitted from electrodes (26, 28) and/or electrodes (32, 34) or electrodes 40 to the back plate.

Figures 6A, 6B:
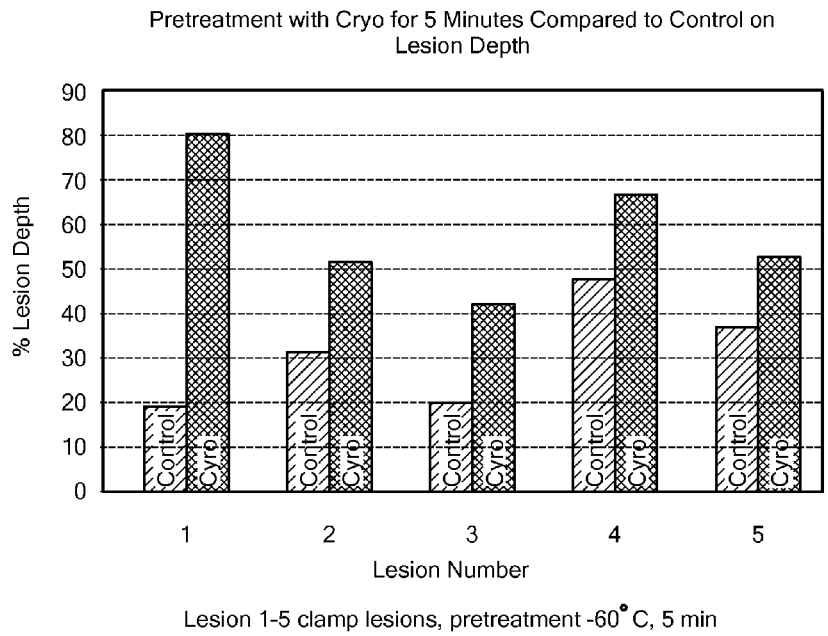
FIG. 6a includes a graph illustrating results of performing an exemplary method on bovine ventricular tissue.
FIG. 6b includes a table below illustrating results of performing an exemplary method on bovine ventricular tissue.

Referring now to FIG. 6a and FIG. 6b, exemplary results of performing the method described with respect to FIG. 5 is shown as applied to bovine ventricular tissue for five separately created lesions. In particular, the graph in FIG. 6a shows a comparison of the lesion depth percentage for tissue measured with bipolar RF energy alone ("control") versus tissue pretreated with cryogenic energy for five minutes at −60° C. then measured with bipolar RF energy ("cryo"). The lesion depth percentage as used herein is the depth of the lesion divided by the tissue thickness multiplied by one hundred, e.g. a 60% lesion has a depth at 60% of the overall tissue depth; 100% is a completely transmural lesion. The table in FIG. 6b compares and tabulates, among other things, the measured reactance of the "control" to the "cryo" treated tissues and the associated two-sided P-values, as well as the percent lesion depth comparison.

As shown in FIGS. 6a and 6b, while there is about a two-fold increase in the percent lesion depth shown in the "cryo" tissue compared to the "control" tissue, the magnitude of the measured impedance of the "control" and "cryo" tissues are virtually the same (20.5Ω for "control" compared to 18.4Ω for "cryo"), with a P-value of 0.09. Because the P-value is greater than 0.05, the hypothesis that these two value are statistically different cannot be accepted. This is so because, as discussed above, once the tissue is necrotic the impedance does not change. Therefore, comparing changes in impedance alone provides no information as to the percent change in the legion depth, because no statistically significant change in impedance is observed. Similarly, the measured resistances of the "control" and "cryo" tissues were virtually the same (18.8Ω for "control" compared to 18.0Ω for "cryo"), with P-value of 0.4. As such, changes in resistance do not show a significant correlation to changes in lesion depth.

Significantly, however, the measured reactance of the "cryo" tissue showed about a two-fold decrease when compared to the measured reactance of the "control" tissue (−8.1Ω for "control" compared to −3.9Ω for "cryo"), with a P-value less than 0.001. Specifically, the results indicate that when the percent lesion depth is about 100% greater in the "cryo" tissue compared to the "control" tissue, the measured reactance of the "cryo" tissue is about 100% less compared to the "control" tissue. Thus, the change in reactance when compared to the change in the lesion depth of the "control" and "cryo" tissues are substantially inversely proportional, such that the change in reactance may be correlated to lesion depth.

Figures 7A, 7B:
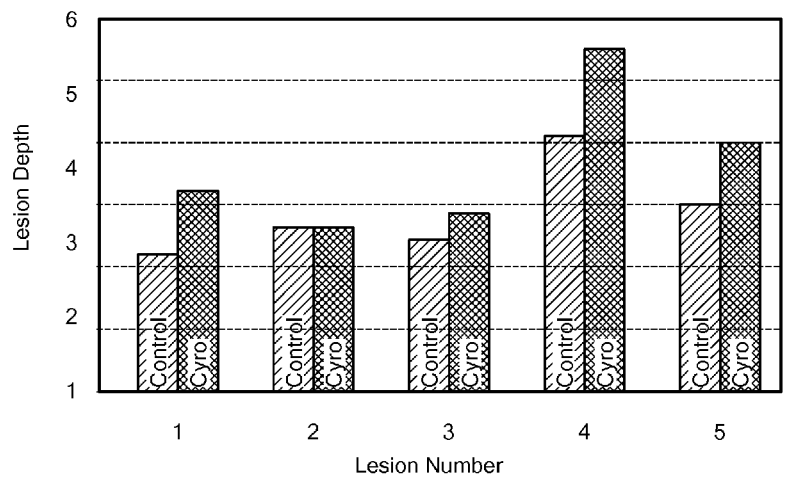
FIG. 7a includes a illustrating results of performing another exemplary method on bovine ventricular tissue.
FIG. 7b includes a table below illustrating results of performing another exemplary method on bovine ventricular tissue.

Referring now to FIGS. 7a and 7b, exemplary results of performing the method described with respect to FIG. 5 are shown as applied to bovine ventricular tissue for five distinct lesions. In this case, the "cryo" tissue is measured with unipolar RF energy instead of bipolar RF energy as shown in FIGS. 6a and 6b. Similar to the results shown in FIGS. 6a and 6b, the change in reactance between the "control" and "cryo" tissues is substantially inversely proportional to the change in the lesion depth. Also, the measured reactance of both "cryo" and "control" lesions were significantly lower than the measured reactance of both "cryo" and "control" lesions created with bipolar RF energy. As such, it is further contemplated that the measuring and correlating of tissue reactance may be used to distinguish unipolar RF ablated regions from bipolar RF ablated regions.

Any of the above methods may be performed not only to distinguish currently treated tissue, but also to identify pretreated tissue or tissue treated or ablated by other modalities. For example, the measured changes in reactance may be used to identify and assess the quality, transmurality, and continuity of lesions created by RF ablation, ultrasound ablation, light ablation, for example, infrared, laser, or visible light energies, chemical ablation, radiation, microwave ablation, electromagnetic radiation, irreversible electroporation, among other ablation modalities. As such, the measured reactance not only provides information as to lesion depth, but also as to the identity of a lesion previously created or to identify gaps in a created lesion. It is further contemplated that in addition to measuring reactance, other measurements that detect the change in the cell membrane thickness may be used to determine lesion quality and transmurality. For example, electroporation may be used to determine lesion quality and transmurality.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of assessing lesion quality of a treated tissue region comprising:
    positioning a medical device proximate the tissue region and circulating a coolant towards a thermally conductive region of the medical device, the medical device having at least two electrodes, the electrodes being positioned proximate the thermally conductive region;
    thermally treating the tissue region;
    inducing a current between the at least two electrodes at a plurality of frequencies;
    measuring the reactance of the thermally treated tissue region at each of the plurality of frequencies;
    defining an untreated tissue reactance value;
    defining a predetermined thermally treated tissue region reactance threshold, the thermally treated tissue region reactance threshold being about a 60-90% reduction in the reactance of the untreated tissue reactance value;
    comparing the measured reactance at each of the plurality of frequencies to the threshold;
    determining the lesion quality of the thermally treated tissue region based on the measured reactance at each of the plurality of frequencies; and
    modifying the thermally treating of the tissue based at least in part on the determination.

2. The method of claim 1, further comprising inducing the current between at least one electrode of the at least two electrodes and a ground electrode.

3. The method of claim 1, wherein the plurality of frequencies includes frequencies selected from at least two of about 10 kHz, 400 kHz, and 1 MHz.

4. The method of claim 1, further comprising assessing lesion continuity based the measured reactance.

5. The method of claim 1, wherein the thermally conductive region includes a balloon, and wherein the balloon is disposed between the at least two electrodes.

6. The method of claim 1, wherein coolant is circulated towards the thermally conductive region of the medical device for about 5 minutes.

7. The method of claim 1, wherein determining the lesion quality of the thermally treated tissue region includes calculating a tissue transmurality based on the comparison of the measured reactance to the threshold.

8. The method of claim 1, further comprising cooling the tissue region to a temperature of about −60° C.

* * * * *